(12) United States Patent
Hu et al.

(10) Patent No.: US 10,246,484 B2
(45) Date of Patent: Apr. 2, 2019

(54) METHOD FOR PURIFYING RECOMBINANT PROTEIN

(71) Applicant: SUNSHINE GUOJIAN PHARMACEUTICAL (SHANGHAI) CO., LTD., Shanghai (CN)

(72) Inventors: Hui Hu, Shanghai (CN); Yunbin Zhu, Shanghai (CN); Meiling Zang, Shanghai (CN)

(73) Assignee: SUNSHINE GUOJIAN PHARMACEUTICAL (SHANGHAI) CO., LTD., Shanghai (CN)

( * ) Notice: Subject to any disclaimer, the term of this patent is extended or adjusted under 35 U.S.C. 154(b) by 375 days.

(21) Appl. No.: 15/034,821

(22) PCT Filed: Nov. 3, 2014

(86) PCT No.: PCT/CN2014/090150
§ 371 (c)(1),
(2) Date: May 5, 2016

(87) PCT Pub. No.: WO2015/067147
PCT Pub. Date: May 14, 2015

(65) Prior Publication Data
US 2016/0289264 A1    Oct. 6, 2016

(30) Foreign Application Priority Data

Nov. 6, 2013 (CN) .......................... 2013 1 0545804

(51) Int. Cl.
*C07K 1/18* (2006.01)
*C07K 16/06* (2006.01)
*C07K 16/32* (2006.01)

(52) U.S. Cl.
CPC .............. *C07K 1/18* (2013.01); *C07K 16/065* (2013.01); *C07K 16/32* (2013.01); *C07K 2317/24* (2013.01)

(58) Field of Classification Search
None
See application file for complete search history.

(56) References Cited

U.S. PATENT DOCUMENTS

| | | | |
|---|---|---|---|
| 6,339,142 B1 * | 1/2002 | Basey | C07K 1/18 424/133.1 |
| 2009/0148435 A1 * | 6/2009 | Lebreton | C07K 1/18 424/130.1 |
| 2012/0065381 A1 * | 3/2012 | Emery | B01D 15/362 530/389.1 |
| 2012/0178910 A1 * | 7/2012 | Arunakumari | C07K 1/18 530/387.3 |
| 2014/0255406 A1 * | 9/2014 | Allan | C07K 16/241 424/136.1 |
| 2014/0323698 A1 * | 10/2014 | Duthe | C07K 1/165 530/387.3 |

FOREIGN PATENT DOCUMENTS

EP    1308455 A2 *    5/2003    ............... C07K 1/18

* cited by examiner

*Primary Examiner* — Daniel E Kolker
*Assistant Examiner* — James L Rogers
(74) *Attorney, Agent, or Firm* — Greer, Burns & Crain, Ltd.

(57) ABSTRACT

A method is provided for purifying a recombinant protein from a mixture comprising the recombinant protein and related proteins, comprising the steps of: A. using a first equilibrating buffer in a first conductivity and pH to make the recombinant protein bind to an ion exchange medium; B. using a second equilibration buffer in a second conductivity and pH to continually equilibrate the ion exchange medium bound to the protein; C. using a washing liquid in a third conductivity and a gradually increasing pH to wash the ion-exchange medium, and eluting the first category-related proteins; D. using a first eluent in a fourth conductivity and pH to elute the ion exchange medium, and eluting the target recombinant protein; and E. using a second eluent in a fifth conductivity and pH to continually elute the ion exchange medium, and eluting the second category-related proteins.

18 Claims, 6 Drawing Sheets

METHOD FOR PURIFYING RECOMBINANT PROTEIN

BACKGROUND

The present invention belongs to the field of protein purification, and more particularly, the invention relates to a method for purifying a recombinant protein.

Ion exchange chromatography is a chromatographic technique that is commonly used for the purification of proteins. In ion exchange chromatography, if the ionic strength of the surrounding buffer is sufficiently low, charged patches on the surface of the solute are attracted by opposite charges attached to a chromatography matrix. Elution is generally achieved by increasing the ionic strength (i.e. conductivity) of the buffer to compete with the solute for the charged sites of the ion exchange matrix. Changing the pH and thereby altering the charge of the solute is another way to is achieve elution of the solute. The change in conductivity or pH may be gradual (gradient elution) or stepwise (step elution). In the past, these changes have been progressive, i.e., the pH or conductivity is increased or decreased in a single direction.

At present, cation chromatography has been used for the purification of proteins in many methods. For example, Chinese patent No. 200410068790.3 discloses that cation exchange chromatography is used for removing acidic contaminants, which comprises increasing the relative conductivity to remove the acidic contaminants, decreasing the conductivity to equilibrate, and then increasing the conductivity to elute. The pH remains constant during the process. The purification results show that the acidic variant content is decreased by about 50%, and basic variants are not mentioned. Chinese patent No. 200880119331.X discloses that cation exchange chromatography is used, which comprises increasing the pH to wash, then decreasing the pH and increasing the conductivity to remove CHOP (Chinese hamster ovary protein), split protein A, DNA, aggregates and so on in the antibody, but does not involves acidic and basic-related proteins in the antibody.

Though the above methods have achieved the purpose of purifying the proteins partially, there still exist some problems of low removal rate of acidic and basic-related proteins and high loss rate of target protein.

SUMMARY

In the present invention, the acidic, basic-related proteins and the target protein are separated by changing the pH and the salt concentration of the buffer. The sample is loaded under the conditions of acidic low pH and relatively high salt concentration solution, and washed and eluted under the conditions of basic high pH and relatively low salt concentration solution. The final removal rate of the acidic-related proteins is greater than 85%, even up to 93%, the removal rate of the basic-related proteins is greater than 59%, and the loss rate of the target protein is less than 26%.

More particularly, the present invention discloses a method for purifying a recombinant protein from a mixture comprising the recombinant protein and its related proteins, which comprises the following steps performed sequentially:

A. binding the recombinant protein to an ion exchange medium using a first equilibration buffer, wherein the first equilibration buffer is at a first conductivity and pH;

B. equilibrating the protein-bound ion exchange medium continually using a second equilibration buffer, wherein the second equilibration buffer is at a second conductivity and pH;

C. washing the ion exchange medium using a wash buffer which has different pHs, so as to elute a first class of the related proteins from the ion exchange medium, wherein the wash buffer is at a third conductivity and a gradually increased pH;

D. washing the ion exchange medium using a first elution buffer, so as to elute the target recombinant protein from the ion exchange medium, wherein the first elution buffer is at a fourth conductivity and pH;

E. washing the ion exchange medium continually using a second elution buffer, so as to elute a second class of the related proteins from the ion exchange medium, wherein the second elution buffer is at a fifth conductivity and pH.

Wherein, the above-mentioned ion exchange medium is a cation exchange medium, refers to a filler having a functional group $SO_3^-$ that is bound to different substrates, which may be but is not limited to: carboxy-methyl-cellulose, BAKERBOND ABX™, sulphopropyl (SP) immobilized on agarose (e.g. SP-SEPHAROSE FAST FLOW™ or SP-SEPHAROSE HIGH PERFORMANCE™ from GE), SOURCE-30S, SOURCE-15S immobilized on Polystyrene/divinyl benzene, Poros HS Poros XS from AB company, sulfonyl immobilized on agarose (e.g. S-SEPHAROSE FAST FLOW™ from Pharmacia) and NUVIA-S, UNO-sphere-S immobilized on hydrophilic polyacrylamides from Bio-rad company, and the like.

The PI (isoelectric point) of the first class of the related proteins is less than that of the recombinant protein, and the PI of the recombinant protein is less than that of the second class of the related proteins. More specifically, the first class of the related proteins is an acidic variant of the recombinant protein, which is defined as a substance which has a less retention time than the target protein on the CEX-HPLC. The second class of the related proteins is an basic variant of the recombinant protein, which is defined as the substance which has a larger retention time than the target protein on the CEX-HPLC.

The conductivity of the second equilibration buffer is less than that of the first equilibration buffer, but the pH of both are the same. Specifically, the first equilibration buffer is a salt-containing buffer, commonly used buffers include PB, MES, acetic acid, and acetic acid buffer is preferred. The concentration of the buffer is controlled in the range of 10-50 mmol/L, and preferably at 20 mmol/L. The pH is controlled in the range of pH 4.0-6.0, and preferably controlled in the range of pH 4.9-5.1, and most preferably at pH 5.0. The types of the salt include sodium chloride, ammonium sulfate, potassium chloride, ammonium chloride, potassium sulfate and so on, and ammonium sulfate is preferred. The concentration of the salt is controlled in the range of 10-70 mmol/L, and preferably controlled in the range of 40-60 mmol/L. The conductivity is controlled in the range of 8-13 ms/cm. The usage of 60 mmol/L ammonium sulfate is more favorable for the efflux of the acidic-related proteins. The second equilibration buffer is a salt-free buffer, commonly used buffers include PB, MES, acetic acid, and acetic acid buffer is preferred. The concentration of the buffer is controlled in the range of 10-50 mmol/L, and preferably at 20 mmol/L. The pH is controlled in the range of pH 4.0-6.0, and preferably controlled in the range of pH 4.9-5.1, and most preferably at pH 5.0. The conductivity is generally in the range of 1-2 ms/cm, and preferably at 1.1 ms/cm.

The conductivity of the wash buffer is less than that of the first equilibration buffer, but the pH of the wash buffer is greater than that of the first and/or second equilibration buffer.

The pH of the first elution buffer is greater than that of the wash buffer, but the conductivity of both are essentially the same. The pH and/or conductivity of the second elution buffer are/is greater than that of the first elution buffer.

The wash buffer and the first elution buffer are achieved by adjusting the mixed ratio of two salt-containing buffers that have different pH. The buffer may be selected from phosphate, HEPES, BICINE and so on, and phosphate is preferred. The concentration of the buffer is controlled in the range of 10-50 mmol/L, and preferably at 10 mmol/L; the conductivity is generally in the range of 1-2 ms/cm, and generally is not controlled. The pH of one buffer A may be at 7.0-7.8, and preferably at 7.5; the pH of one buffer B may be at 9.3-9.4. The types of salt include sodium chloride, ammonium sulfate, potassium chloride, ammonium chloride, potassium sulfate and the like. More specifically, the change of pH of the wash buffer and the first elution buffer is achieved by changing 25% $Na_2HPO_4$ pH 7.5+75% $Na_2HPO_4$ pH 9.3-9.4 to 15% $Na_2HPO_4$ pH 7.5+85% $Na_2HPO_4$ pH 9.3-9.4.

The second elution buffer is a high-salt aqueous solution, the types of the salt include sodium chloride, ammonium sulfate, potassium chloride, ammonium chloride, potassium sulfate and the like, and sodium chloride is preferred.

Various buffers are stored generally at 4-30 degree Celsius, and preferably at 4-8 degree Celsius.

After the recombinant protein, preferably recombinant antibody (e.g. recombinant anti-HER2 antibody) is expressed by CHO cells, the supernatant is collected by disc centrifuge technique and deep filtration, and then eluted with citric acid at acidic pH by protein-A affinity chromatography, to obtain a homogeneous mixture comprising the target protein and the acidic, basic-related proteins. Such mixture is the sample loading solution of the cation chromatography (e.g. Nuvia-S).

The sample loading solution is adjusted to pH 4.0-6.0, preferably to pH 4.9-5.1, and most preferably at pH 5.0, using an basic substance such as TRIS-base/sodium hydroxide. After the completion of pH adjustment, a salt for salting out such as sodium chlorine/ammonium sulfate is added to adjust the conductivity, using a temperature-compensated conductivity meter, such as seven-easy conductivity meter from Mettler company, and using 20 degree Celsius as the reference temperature. The conductivity is adjusted and controlled in the range of 6.0-18.0 ms/cm, and preferably in the range of 8.0-12.5 ms/cm.

Two different sample loading conductivities are used in the present invention, one is 8.4 ms/cm, and the other is 12.0 ms/cm. Under the same pH, when the sample is loaded at a high conductivity, it is favorable for the efflux of the acidic-related proteins, and generally about 10-20% of acidic peak is flowed out and the loss of the target protein is negligible. After the adjustment of the pH and conductivity, the sample is stored at 4 degree Celsius, which can slow the further hydrolysis of the target protein.

The chromatography column that is packed has to meet the usage requirements. Generally the column efficiency is controlled at a plate number per meter of 2000 or more. The chromatography flow rate is generally controlled at 5 cm/min. The load capacity of the chromatography column is controlled at 10-20 mg/ml, and preferably at 15 mg/ml. The protein is quantified using a spectrophotometer at 280 nm UV, and the extinction coefficient of the recombinant antibody, such as anti-HER2 humanized monoclonal antibody, is 1.50.

With respect to the chromatography control, the first equilibration buffer is used to equilibrate the column, generally 3CV is enough to complete the equilibration and then sample is loaded. After loading the sample, the column is continually equilibrated using at least 1CV of the first equilibration buffer, then equilibrated using at least 1 CV of the second equilibration buffer; such a step is intended to remove the salt in the equilibration buffer, so as to avoid its influence on the washing step. Then, 2CV of 100% A wash buffer is used to wash the column to increase the pH. 60% B-75% B wash buffer is used to wash the chromatography column to remove the acidic-related proteins. The washing step may be a single-step wash or multi-step wash; generally at least a single-step wash with 75% B is used, while a multi-step wash is more favorable to remove the acidic-related proteins. The pH of wash buffer is generally at 7.6-7.9. The washing process usually lasts 20-30CV. When the wash peak dropped to about 50 mAu, it can be considered the end of the washing process. Elution is performed using the first elution buffer containing 85% B, and the pH of elution buffer is generally between 8.05-8.15. The elution process generally lasts 8-15CV. When the elution peak dropped to about 50 mAu, it can be considered the end of the elution process. Finally, the second elution buffer is used to elute the basic-related proteins.

The proportion of the acidic-related proteins in the loading sample is controlled below 50%, the lower the better. The proportion of the basic peaks is controlled below 20%, the lower the better. By chromatography, the CEX-HPLC purity of the target protein at the main peak can be increased from 37% to above 70%, and the purity can be further increased to 75% or even above 77% when a multi-step washing mode or a flow-through mode is used. The yield of the target protein is generally more than 74%.

In the present invention, the recombinant protein is a protein that is produced in a host cell. The host cell has been transformed or transfected with nucleic acid encoding the protein, or produces the protein as a result of homologous recombination. "Transformation" and "transfection" are used interchangeably to refer to the process of introducing nucleic acid into a cell. Following transformation or transfection, the nucleic acid may integrate into the host cell genome, or may exist as an extrachromosomal element. The "host cell" includes a cell in in vitro cell culture as well a cell within a host animal. For example, methods for recombinant production of polypeptides are described in U.S. Pat. No. 5,534,615 (incorporated herein by reference).

The recombinant protein in the present invention mainly refers to an antibody, particularly refers to all recombinant antibody that binds HER2 antigen, including but not limited to trastuzumab (Carter et al., Proc. Natl. Acad. Sci. USA, 89: 4285-4289 (1992)), pertuzumab (OMNITARG™) (WO01/00245), and all antibody proteins mentioned in U.S. Pat. No. 64,072,135, U.S. Pat. No. 5,821,337, U.S. Pat. No. 6,639,055, U.S. Pat. No. 6,719,971, U.S. Pat. No. 6,800,738, U.S. Pat. No. 6,054,297, U.S. Pat. No. 5,677,171, U.S. Pat. No. 5,770,195, U.S. Pat. No. 5,720,954, U.S. Pat. No. 5,772,997, U.S. Pat. No. 6,165,464, U.S. Pat. No. 6,387,371, U.S. Pat. No. 6,399,063, U.S. Pat. No. 5,720,937, U.S. Pat. No. 5,725,856 and Chinese Patent CN 01132225.X. The "HER2 antigen" herein refers to human HER2 protein, such as the human HER2 proteins described in Semba et al., PNAS (USA) 82:6497-6501 (1985) and Yamamoto et al., Nature 319:230-234 (1986) (Genebank accession number X03363).

The acidic-related protein is a variant of a target recombinant protein which is more acidic (e.g. as determined by cation exchange chromatography) than the target recombinant protein. An example of an acidic-related protein is a deamidated variant.

The basic-related protein is a variant of a target recombinant protein which is more basic (e.g. as determined by cation exchange chromatography) than the target recombinant protein. An example of an basic-related protein is that C-terminal lysine is not completely removed, N terminal GLN (Glutamine) is not completely cyclizated.

The term "mixture" in reference to a composition comprising an antibody (preferably anti-HER2 antibody) means the presence of the desired antibody and one or more acidic variants and basic variants thereof. The acidic variants may comprise predominantly deamidated anti-HER2 antibody, with minor amounts of other acidic variants. It has been found, for example, that in preparations of anti-HER2 antibody obtained from recombinant expression, as much as about 50% of the anti-HER2 antibody is deamidated, and about 15% of the antibody is an basic-related protein.

The "cation exchange resin" refers to a solid phase which is negatively charged, and which thus has free cations for exchange with cations in an aqueous solution passed over or through the solid phase. A negatively charged ligand attached to the solid phase to form the cation exchange resin may be a carboxylate or sulfonate, for example. Commercially available cation exchange resins refer to filler having a functional group $SO_3^-$ that is bound to different substrates, and include but not limited to carboxy-methyl-cellulose, BAKERBOND ABX™, sulphopropyl (SP) immobilized on agarose (e.g. SP-SEPHAROSE FAST FLOW™ or SP-SEPHAROSE HIGH PERFORMANCE™ from GE), SOURCE-30S, SOURCE-15S immobilized on Polystyrene/divinyl benzene, Poros HS Poros XS from AB company, sulfonyl immobilized on agarose (e.g. S-SEPHAROSE FAST FLOW™ from Pharmacia) and NUVIA-S, UNOsphere-S immobilized on hydrophilic polyacrylamides from Bio-rad company, and the like.

The "buffer" is a solution that resists changes in pH by the action of its acid-base conjugate components. Various buffers which can be employed depending, for example, on the desired pH of the buffer are described in Buffers A Guide for the Preparation and Use of Buffers in Biological Systems, Gueffroy, D, Ed Calbiochem Corporation (1975). In one embodiment, the buffer has a pH in the range from about 5 to about 7 (e.g. as in Example 1 below). Examples of buffers that will control the pH in this range include MES, MOPS, MOPSO, phosphate, acetate, citrate, succinate, and ammonium buffers, as well as combinations of these.

The "loading buffer" is that which is used to load the composition comprising the target protein molecule and one or more related proteins onto the ion exchange resin. The loading buffer has a conductivity and/or pH such that the target protein molecule (and generally one or more contaminants) is/are bound to the ion exchange resin.

The "wash buffer" is used to elute one or more related proteins from the ion exchange resin, prior to eluting the target protein. The conductivity and/or pH of the wash buffer are/is such that the related protein is eluted from the ion exchange resin, but the amount of the eluted target protein is very small.

The "elution buffer" is used to elute the target protein from the solid phase. The conductivity and/or pH of the elution buffer are/is such that the target protein is eluted from the ion exchange resin.

Conductivity refers to the ability of an aqueous solution to conduct an electric current between two electrodes. In solution, the current flows by ion transport. Therefore, with an increasing amount of ions present in the aqueous solution, the solution will have a higher conductivity. The unit of measurement for conductivity is mmhos/cm (ms/cm), and can be measured using a conductivity meter (e.g., sold by Orion). The conductivity of a solution may be altered by changing the concentration of ions therein. For example, the concentration of a buffering agent and/or concentration of a salt (e.g. NaCl or KCl) in the solution may be altered in order to achieve the desired conductivity.

DETAILED DESCRIPTION

Figure 1:
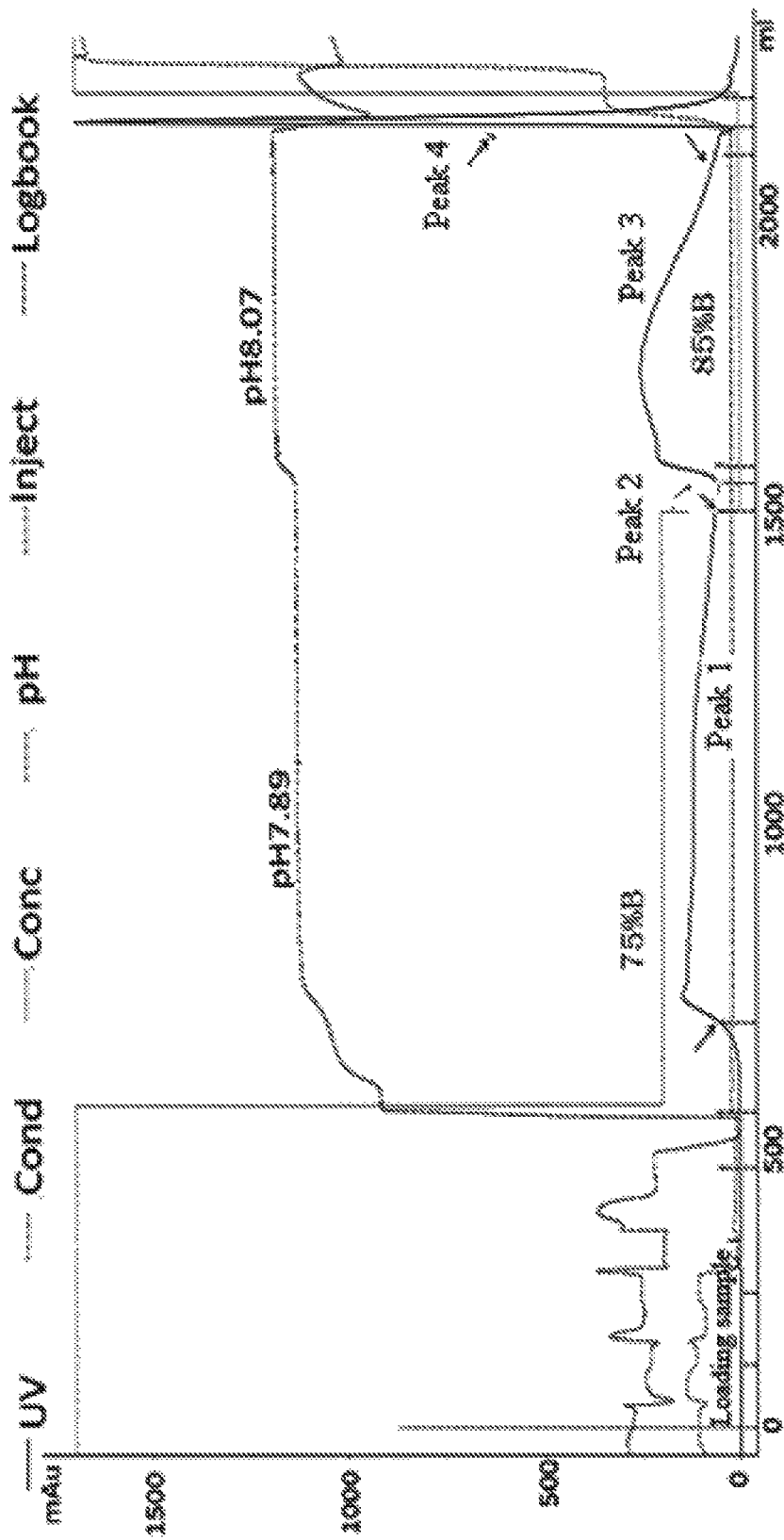
FIG. 1: chromatogram of the final product obtained in Example 1.

The following examples are only provided to further describe the invention, and should not to be construed as limiting the invention in anyway.

Example 1

The binding mode, single-step wash with 75% B, single-step elution with 85% B were used.

Chromatography column: XK16/40, NuviaS, 1CV=50 ml, H=25 cm, flow=10 ml min

Chromatography system: AKTA-PURIFIER

Operating software: unicorn System

Sample: A mixture of rhuMAb HER2 antibody and the related proteins, was replaced by r-proteinA chromatography to the citric acid system, and then adjusted to pH 5.0 with TRIS-base. Sodium chloride was added to adjust the conductivity to 8.5 ms/cm. The load capacity was 15 mg/ml. The total loading sample was 750 mg.

Solutions:

Equilibration buffer 1: 20 mmHAC-NaOH+40 mm ammonium sulfate, pH 5.0, conductivity 8.4 ms/cm Equilibration buffer 2: 20 mmHAC-NaOH, pH 5.0, conductivity 1.1 ms/cm Solution A: 10 mmNa$_2$HPO$_4$+phosphoric acid, pH 7.52, conductivity 1.5 ms/cm Solution B: 10 mmNa$_2$HPO$_4$+phosphoric acid, pH 9.36, conductivity 1.5 ms/cm Wash buffer 1: 100% A Wash buffer 2: 25% A+75% B Elution buffer 1: 15% A+85% B Elution buffer 2: 300 mmol/L NaCl, conductivity 26 ms/cm Operation Flow:

Equilibration buffer 1 (3CV)—Loading—Equilibration buffer 1 (1CV)—Equilibration buffer 2 (2CV)—Wash buffer 1 (2CV)—Wash buffer 2 (20CV)—Elution buffer 1 (12CV))—Elution buffer 2 (2CV)—2N sodium chloride (2CV)—Purified water (1CV)—0.1N sodium hydroxide (3CV) CV=column bed Collected peak: Protein content: The protein concentration of each fraction was measured by scanning each sample using a spectrophotometer (Loading sample, Peak 1, Peak 2, Peak 3, Peak 4). The recovery content of the product was calculated according to the results.

Peak 1 (wash peak): 0.855 L*0.37 mg/ml=316.35 mg

Peak 2 (prior to main peak): 27 ml*0.31 mg/ml=8.37 mg

Peak 3 (main peak): 520 ml*0.6 mg/ml=312 mg

Peak 4 (eluted with 300 mm sodium chloride): 50 ml*1.96 mg/ml=98 mg

Total recovery rate was: 734.72/752*100%=97.7%

Yield of main peak: 41.48%

Figure 2:
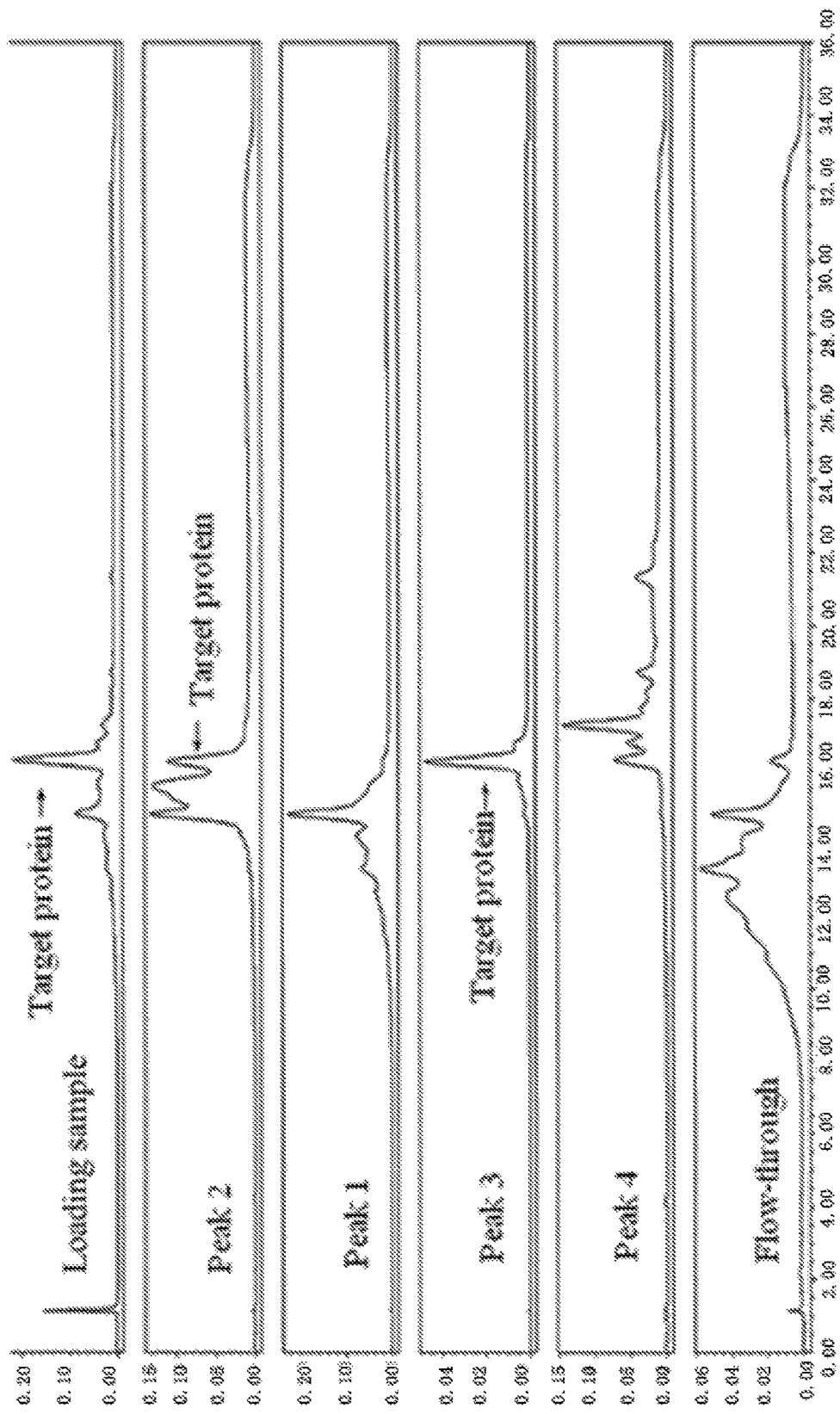
FIG. 2: CEX-HPLC of each fraction obtained in Example 1.

Yield analysis of target peak (CEX-HPLC) is shown in FIG. 2, and the related data are shown in Table 1.

TABLE 1

| Sample name | Content mg | Acidic peak ratio | Main peak ratio | Basic peak ratio | Total content of acidic peak | Total content of main peak | Total content of basic peak | Yield of target peak | Remark |
|---|---|---|---|---|---|---|---|---|---|
| Loading sample | 750 | 47.90% | 37.51% | 14.59% | 359.25 | 281.33 | 109.43 | | |
| Peak 1 | 316.35 | 97.43% | 2.57% | 0% | 308.22 | 8.13 | 0.00 | 2.89% | Wash peak |
| Peak 2 | 8.37 | 75.41% | 21.89% | 2.70% | 6.31 | 1.83 | 0.23 | 0.65% | Prior to main peak |
| Peak 3 | 312 | 17.15% | 69.99% | 12.86% | 53.51 | 218.37 | 40.12 | 77.62% | Main peak |
| Peak 4 | 98 | 2.74% | 13.55% | 83.71% | 2.69 | 13.28 | 82.04 | 4.72% | Peak II |

The chromatogram is shown in FIG. 1.
The results are as follows:
When the method in which the binding mode, single-step wash with 75% B and single-step elution with 85% B were used, the purity of the target peak can be increased from 37.51% to 69.99%, wherein:

Removal rate of acidic peak: (1-53.15/359.25)*100%=85.22%
Removal rate of basic peak: (1-40.12/109.43)*100%=63.4%
Loss rate of target peak: (1-218.37/281.33)*100%=22.38%.

Example 2

Figure 4:
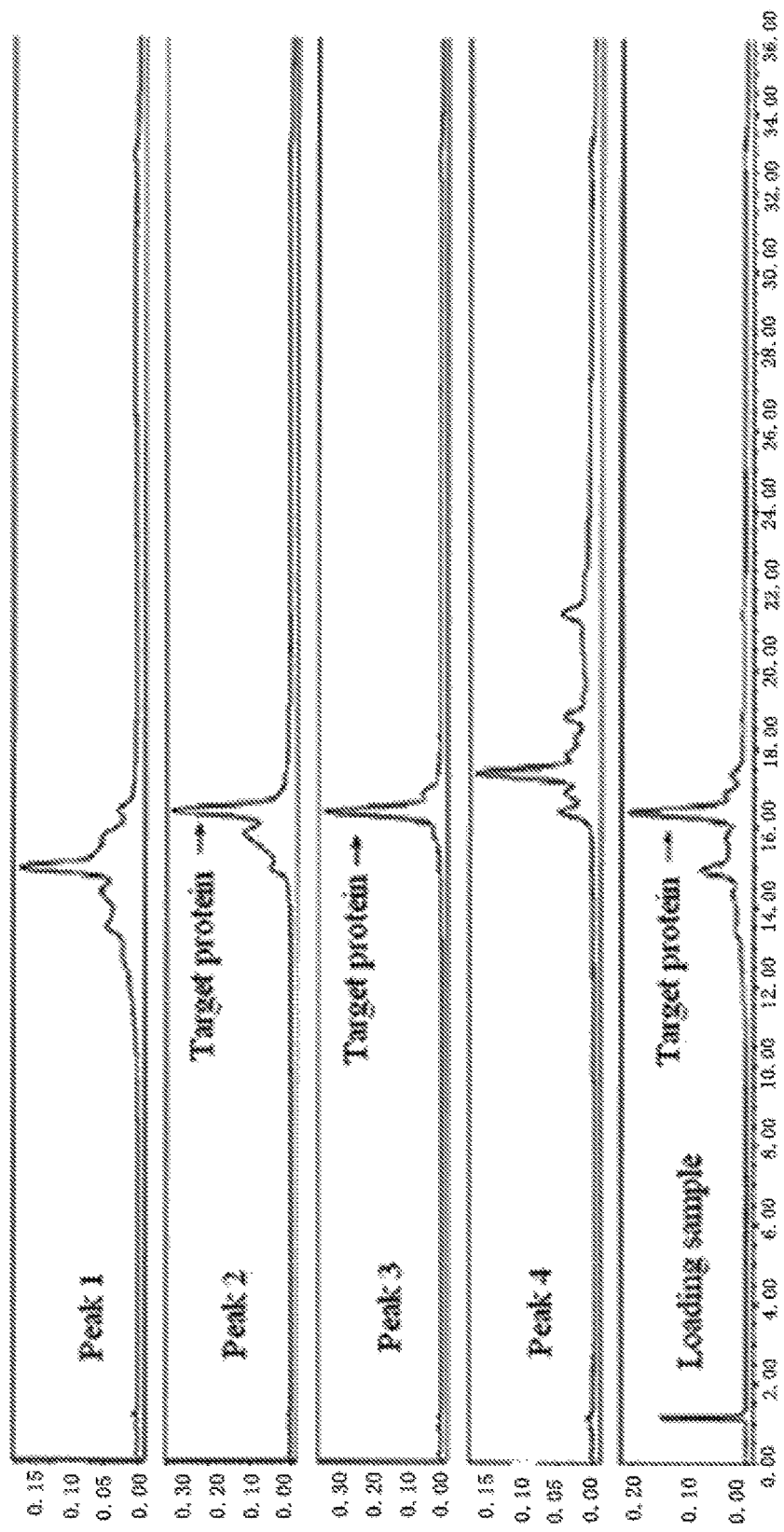
FIG. 4: CEX-HPLC of each fraction obtained in Example 2.

The binding mode, multi-step wash with 60% B-70% B-75% B, and single-step elution with 85% B were used
Chromatography column: XK16/40, NuviaS, 1CV=50 ml, H=25 cm, flow=10 ml/min
Chromatography system: AKTA-PURIFIER
Operating software: unicorn System
Sample: A mixture of rhuMAb HER2 antibody and the related proteins, was replaced by r-proteinA chromatography to the citric acid system, and then adjusted to pH 5.0 with TRIS-base. Sodium chloride was added to adjust the conductivity to 8 ms/cm. The load capacity was 15 mg/ml. The total loading sample was 745 mg.
Solutions:
Equilibration buffer 1: 20 mmHAC-NaOH+40 mm ammonium sulfate, pH 5.0, conductivity 8.4 ms/cm
Equilibration buffer 2: 20 mmHAC-NaOH, pH 5.03, conductivity 1.1 ms/cm
Solution A: 10 mm$Na_2HPO_4$+phosphoric acid, pH 7.52, conductivity 1.5 ms/cm
Solution B: 10 mm$Na_2HPO_4$+phosphoric acid, pH: 9.36, conductivity 1.5 ms/cm
Wash buffer 1: 100% A
Wash buffer 2: 40% A+60% B
Wash buffer 3: 30% A+70% B
Wash buffer 4: 25% A+75% B
Elution buffer 1: 15% A+85% B
Elution buffer 2: 300 mmol/L NaCl, conductivity 26 ms/cm
Operation Flow:
Equilibration buffer 1 (3CV)—Loading—Equilibration buffer 1 (1CV)—Equilibration buffer 2 (2CV)—Wash buffer 1 (2CV)—Wash buffer 2-4 equal gradient (60% B (5CV)—70% B (7CV)—75% B (12CV))—Elution buffer 1 85% B (9CV))—Elution buffer 2 (2CV)—2N sodium chloride (2CV)—Purified water (1CV)—0.1N sodium hydroxide (3CV)
Collected peaks are as follows:
Peak 1 (wash peak, including all peaks prior to wash with 75% B): 1.1 L*0.31 mg/ml=341 mg
Peak 2 (prior to main peak, eluted with 85% B to 150 mau): 28 ml*0.3 mg/ml=8.4 mg
Peak 3 (main peak, eluted with 85% B from 150 mau to 50 mau): 367 ml*0.77 mg/ml=282.59 mg
Peak 4 (eluted with 300 mm sodium chloride): 53 ml*1.48 mg/ml=78.44 mg
Total recovery rate: 710.43/7458*100%=95.35%
Yield of main peak: 37.95%
Yield analysis of target peak (CEX-HPLC) is shown in FIG. 4, and the related data are shown in Table 2.

TABLE 2

| Sample name | Content mg | Acidic peak ratio | Main peak ratio | Basic peak ratio | Total content of acidic peak | Total content of main peak | Total content of basic peak | Yield of target peak | Remark |
|---|---|---|---|---|---|---|---|---|---|
| Loading sample | 745.8 | 48.02% | 37.53% | 14.45% | 358.13 | 279.90 | 107.77 | | |
| Peak 1 | 341 | 94.24% | 5.59% | 0.17% | 321.36 | 19.06 | 0.58 | 6.81% | Wash peak |
| Peak 2 | 8.4 | 44.67% | 46.85% | 8.48% | 3.75 | 3.94 | 0.71 | 1.41% | prior to main peak |
| Peak 3 | 282.59 | 9.47% | 75.15% | 15.38% | 26.76 | 212.37 | 43.46 | 75.87% | Main peak |
| Peak 4 | 78.44 | 0.58% | 9.40% | 90.02% | 0.45 | 7.37 | 70.61 | 2.63% | Peak II |

Figure 3:
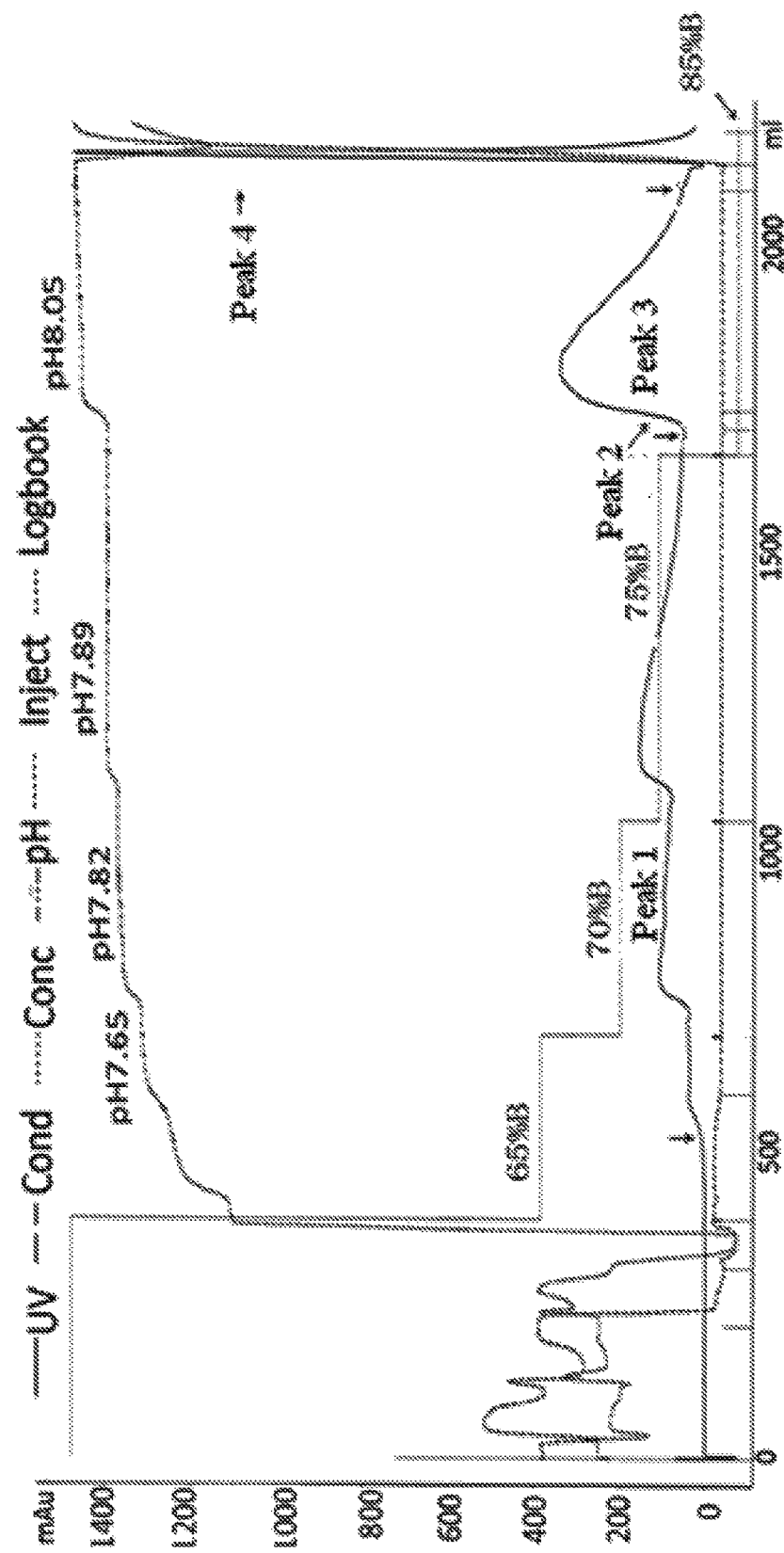
FIG. 3: chromatogram of the final product obtained in Example 2.

The chromatogram is shown in FIG. 3.

The results are as follows:

When the method in which the binding mode, multi-step wash with 60% B—70% B—75% B and single-step elution with 85% B were used, the purity of the target peak can be increased from 37.53% to 75.15%, wherein:

Removal rate of acidic peak: (1-26.76/358.13)*100%=92.53%

Removal rate of basic peak: (1-43.46/107.77)*100%=59.67%

Loss rate of target peak: (1-212.37/279.90)*100%=24.13%.

Example 3

The flow-through mode, single-step wash with 75% B, and single-step elution with 85% B were used Chromatography column: XK16/40, NuviaS, 1CV=50 ml, H=25 cm, flow=10 ml/min Chromatography system: AKTA-PURIFIER Operating software: unicorn System Sample: A mixture of rhuMAb HER2 antibody and related proteins, was replaced by r-proteinA chromatography to the citric acid system, and then adjusted to pH 5.0 with TRIS-base. Sodium chloride was added to adjust the conductivity to 12 ms/cm. The load capacity was 15 mg/ml. The total loading sample was 753.28 mg.

Solutions:

Equilibration buffer 1: 20 mmHAC-NaOH+60 mm ammonium sulfate, pH 5.0, conductivity 12 ms/cm Equilibration buffer 2: 20 mmHAC-NaOH, pH 5.0, conductivity 0.9 ms/cm Solution A: 10 mm$Na_2HPO_4$+phosphoric acid, pH 7.50, conductivity 1.5 ms/cm Solution B: 10 mm$Na_2HPO_4$+phosphoric acid, pH 9.36, conductivity 1.5 ms/cm Wash buffer 1: 100% A Wash buffer 2: 25% A+75% B Elution buffer 1: 15% A+85% B Elution buffer 2: 300 mmol/L NaCl, conductivity 26 ms/cm Operation Flow:

Equilibration buffer 1 (3CV)—Loading—Equilibration buffer 1 (1CV)—Equilibration buffer 2 (2CV)—Wash buffer 1 (2CV)—Wash buffer 2 (30CV)—Elution buffer 1 (11CV)—Elution buffer 2 (2CV)—2N sodium chloride (2CV)—Purified water (1CV)—0.1N sodium hydroxide (3CV)

Collected peaks: Protein content: The protein concentration of each fraction was measured by scanning each sample using a spectrophotometer. (Loading sample, Peak 1, Peak 2, Peak 3, Peak 4, Peak 5). The recovery content of the product was calculated according to the results.

Peak 1 (flow-through peak): 150 ml*0.1004 mg/ml=15.06 mg

Peak 2 (wash peak): 807 ml*0.4388 mg/ml=354.19 mg

Peak 3 (prior to main peak): 60 ml*0.13 mg/ml=8 mg

Peak 4 (main peak): 418 ml*0.6507 mg/ml=272 mg

Peak 5 (eluted with 300 mm sodium chloride): 51 ml*1.96 mg/ml=100 mg

Total recovery rate: 749.25/753.28*100%=99.46%

Yield of the main peak: 36.11%

Figure 6:
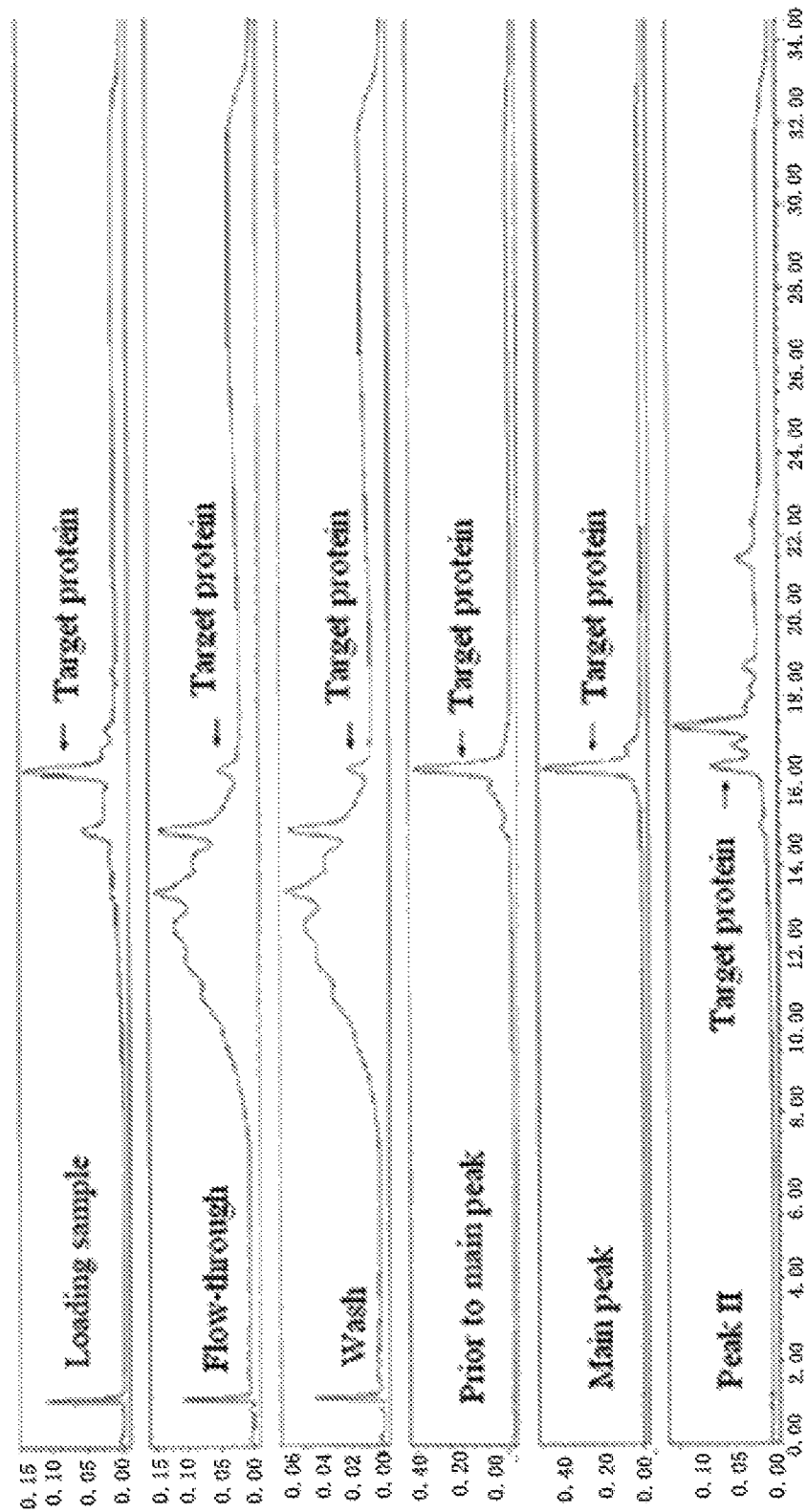
FIG. 6: CEX-HPLC of each fraction obtained in Example 3.

Yield analysis of the target peak (CEX-HPLC) is shown in FIG. 6, and the related data are shown in Table 3.

TABLE 3

| Sample name | Content mg | Acidic peak ratio | Main peak ratio | Basic peak ratio | Total content of acidic peak | Total content of main peak | Total content of basic peak | Yield of target peak | Remark |
|---|---|---|---|---|---|---|---|---|---|
| Loading sample | 753.26 | 47.60% | 37.59% | 14.81% | 358.56 | 283.16 | 111.56 | | |
| Peak 1 | 15.06 | 97.23% | 2.41% | 0.36% | 14.64 | 0.36 | 0.05 | 0.13% | Flow-through peak |
| Peak 2 | 354.19 | 97.30% | 2.50% | 0.02% | 344.63 | 8.85 | 0.07 | 3.13% | Wash peak |
| Peak 3 | 8 | 31.71% | 63.19% | 5.10% | 2.54 | 5.06 | 0.41 | 1.79% | Prior to main peak |
| Peak 4 | 272 | 8.19% | 77.34% | 14.46% | 22.28 | 210.36 | 39.33 | 74.29% | Main peak |
| Peak 5 | 100 | 4.30% | 15.49% | 80.19% | 4.30 | 15.49 | 80.19 | 5.47% | Peak II |

Figure 5:
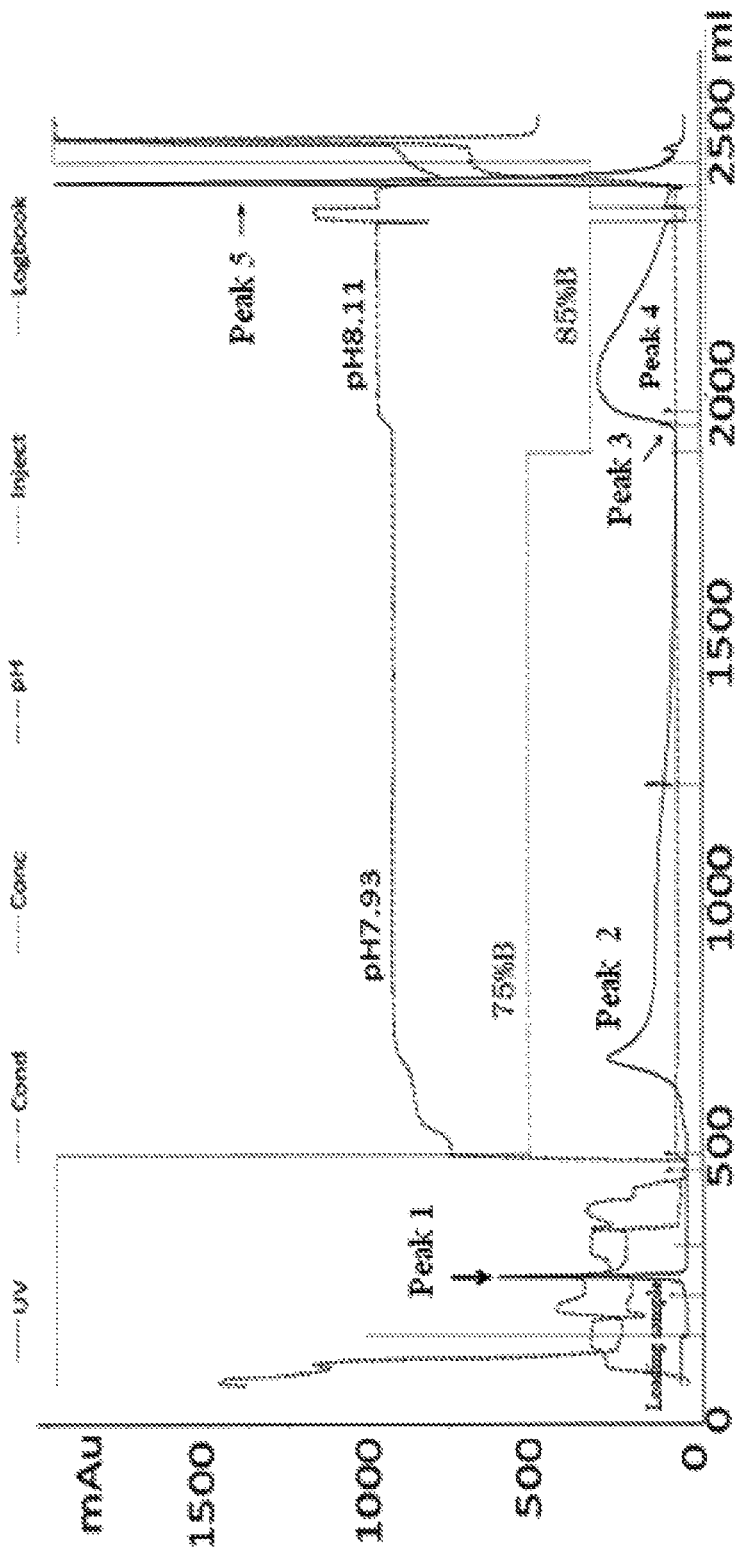
FIG. 5: chromatogram of the final product obtained in Example 3.

The chromatogram is shown in FIG. 5.

The results are as follows:

When the method in which the flow-through mode, single-step wash with 75% B, and single-step elution with 85% B were used, the purity of the target peak can be increased from 37.59% to 77.34%, wherein:

Removal rate of acidic peak: (1-22.28/358.56)*100%=93.78%

Removal rate of basic peak: (1-39.33/111.56)*100%=64.75%

Yield rate of target peak: (1-210.36/281.36)*100%=25.23%.

Compared to Examples 1 and 2, Example 3 can be more efficient to remove acidic peak and basic peak, but will make the target protein yield slightly decreased. Examples 1-3 show the high efficiency effect of the combination of loading at relatively low pH and high salt concentration, washing and eluting at relatively high pH and low salt concentration on the separation of a recombinant protein and its related proteins.

The mixture of rhuMAb HER2 antibody and its related proteins in above Examples 1-3 were obtained as follows: Full length human IgG rhuMAb HER2, which comprises the light chain amino acid sequence of SEQ ID NO: 1 and heavy chain amino acid sequence of SEQ ID NO: 2 mentioned in Chinese Patent No. 200410068790.3, was produced recombinantly in CHO cells (Carter et al., Proc. Natl. Acad. Sci. USA, 89: 4285-4289(1992). After the recombinant antibody was expressed by CHO cells, the supernatant, which was a mixture of HER2 rhuMAb antibody and its related proteins, was collected by disc centrifuge technique and deep filtration.

The present applicant also prepared samples according to the above method using rhuMAB HER2 antibody sequence mentioned in U.S. Pat. No. 64,072,135, U.S. Pat. No. 5,821,337 and Chinese Patent CN 01132225.X, and performed test and verification according to the same method as Examples 1-3, and the final results and conclusions were basically the same.

Detection and analysis method in Examples 1-3: CEX-HPLC is described in detail as follows:

1. Reagents and Instruments

The purity level of all chemical reagents was at least as analytical.

1.1 Carboxypeptidase B: at a concentration of 5 mg/mL 1.2 1 mol/L Tris.HCl solution: pH 7.4-7.6

1.3 20 mmol/L phosphate buffer: pH 6.4-6.6

1.4 20 mmol/L phosphate buffer+200 mmol/L NaCl: pH6.4-6.6

1.5 High performance liquid chromatography instrument: Waters Alliance 2998+2695, Ultimate 3000B series or other similar liquid chromatography instruments.

1.6 Chromatography column: DionexPropac WCX-10 (4×250 mm)

2 Test Procedures 2.1 Treatment of test sample 2.1.1 Enzyme digestion treatment of Carboxypeptidase B: The test sample was subjected to enzyme digestion treatment. The reaction volume was 100-500 uL, containing 5 mg/mL of anti-HER2 rhMAb sample, 10% (V/V) 1 mol/L Tris-HCl buffer pH 7.5 and 2% (V/V) Carboxypeptidase B (5 mg/mL), reacted at 37° C. in water bath for 3 hours.

2.1.2 Dilution before sampling: The reaction solutions in the prior step were all diluted to 1.0 mg/mL with 20 mmol/L phosphate buffer (pH6.4-6.6), and centrifuged at 12000 r/min for 10 min, and the supernatant was taken for sampling.

2.2 Chromatographic conditions 2.2.1 Column temperature: 40±2.0° C.

2.2.2 Sample temperature: 5±3.0° C.

2.2.3 Detection wavelength: 214 nm 2.2.4 Sample volume: 10 uL 2.2.5 Flow rate: 1.0 mL/min 2.2.6 Mobile phase: A: 20 mmol/L phosphate buffer (pH6.4-6.6); B: 20 mmol/L phosphate buffer (pH 6.4-6 6)+200 mmol/L NaCl. After preparation, it was subjected to filtration by 0.22 um filter membrane, followed by ultrasonic treatment and deaeration, and stored at 2-8 degree Celsius.

2.2.7 Gradient table of mobile phase

| No. | Time (min) | Flow-rate (ml/min) | A (%) | B (%) |
|---|---|---|---|---|
| 1 | 0 | 1 | 90 | 10 |
| 2 | 5 | 1 | 90 | 10 |
| 3 | 25 | 1 | 50 | 50 |
| 4 | 30 | 1 | 50 | 50 |
| 5 | 31 | 1 | 90 | 10 |
| 6 | 36 | 1 | 90 | 10 |

3. Result analysis

The chromatogram is processed according to the integral software, calculated according to peak area normalization method, and the purity report is issued.

What is claimed is:

1. A method for purifying a recombinant protein from a mixture comprising the recombinant protein and its related proteins, which comprises the following steps performed sequentially:

A. binding the recombinant protein to an ion exchange medium using a first equilibration buffer, wherein the first equilibration buffer is at a first conductivity and pH;

the ion exchange medium is a cation exchange medium;

B. equilibrating the protein-bound ion exchange medium continually using a second equilibration buffer, wherein the second equilibration buffer is at a second conductivity and pH;

the conductivity of the second equilibration buffer is less than that of the first equilibration buffer, but the pH of both are the same;

C. washing the ion exchange medium using a wash buffer which has different pH, so as to elute a first class of the related proteins from the ion exchange medium, wherein the wash buffer is at a third conductivity and a gradually increased pH;

the conductivity of the wash buffer is less than that of the first equilibration buffer, but the pH of the wash buffer is greater than that of the first and/or second equilibration buffer;

D. washing the ion exchange medium using a first elution buffer, so as to elute the target recombinant protein from the ion exchange medium, wherein the first elution buffer is at a fourth conductivity and pH;

the pH of the first elution buffer is greater than that of the wash buffer, but the conductivity of both are essentially the same; and E. then washing the ion exchange medium using a second elution buffer, so as to elute a second class of related proteins from the ion exchange medium, wherein the second elution buffer is at a fifth conductivity and pH;

the pH and/or conductivity of the second elution buffer are/is greater than that of the first elution buffer.

2. The method of claim 1, characterized in that, the cation exchange medium is a filler having a functional group $SO_3^-$ that is bound to different substrates.

3. The method of claim 1, characterized in that, the elution of the first class of the related proteins and the target protein is achieved by changing the pH of the wash buffer and the first elution buffer.

4. The method of claim 3, characterized in that, the change of pH of the wash buffer and the first elution buffer is achieved by adjusting the mixed ratio of two salt-containing buffers that have different pH.

5. The method of claim 4, characterized in that, the change of pH of the wash buffer and the first elution buffer is achieved by changing 25% $Na_2HPO_4$ pH7.5+75% $Na_2HPO_4$ pH9.3-9.4 to 15% $Na_2HPO_4$ pH7.5+85% $Na_2HPO_4$ pH9.3-9.4.

6. The method of claim 1, characterized in that, in steps A-D, the pH is gradually increased.

7. The method of claim 1, characterized in that, the recombinant protein and its related proteins have different PI, wherein the PI of the first class of the related proteins is less than that of the recombinant protein, and the PI of the recombinant protein is less than that of the second class of related proteins.

8. The method of claim 1, characterized in that, the first class of the related proteins is an acidic variant of the recombinant protein, which is defined as a substance which has a less retention time than the target protein on CEX-HPLC; the second class of the related protein is a basic variant of the recombinant protein, which is defined as a substance which has a greater retention time than the target protein on CEX-HPLC.

9. The method of claim 1, characterized in that, the recombinant protein is an antibody.

10. The method of claim 9, characterized in that, the antibody is selected from the group consisting of trastuzumab, pertuzumab and other HER2 antigen-binding recombinant antibodies.

11. The method of claim 1, characterized in that, the method further comprises subjecting the mixture comprising the recombinant protein and its related proteins to one or more purification steps, either before, during, or after the ion exchange chromatography, so as to obtain a homogeneous preparation of the recombinant protein.

12. A method for purifying a recombinant anti-HER2 antibody from a mixture comprising the recombinant anti-HER2 antibody and its related proteins, which comprises the following steps performed sequentially:
   a). binding the recombinant protein to a cation exchange medium using a first equilibration buffer, wherein the first equilibration buffer is at a first conductivity and pH;
   b). then equilibrating the protein-bound cation exchange medium using a second equilibration buffer, wherein the second equilibration buffer is at a second conductivity and pH;
   c). washing the ion exchange medium using a wash buffer which has different pH, so as to elute the first class of the related proteins from the cation exchange medium, wherein the wash buffer is at a third conductivity and a gradually increased pH;
   d). washing the ion exchange medium using a first elution buffer, so as to elute the target recombinant protein from the cation exchange medium, wherein the first elution buffer is at a fourth conductivity and pH; and
   e). washing the ion exchange medium using a second elution buffer, so as to elute the second class of the related proteins from the cation exchange medium, wherein the second elution buffer is at a fifth conductivity and pH;
   the conductivity of the wash buffer is less than that of the first equilibration buffer, but the pH of the wash buffer is greater than that of the first and/or second equilibration buffer; the pH of the first elution buffer is greater than that of the wash buffer, and the conductivity of the first elution buffer is basically the same as that of the wash buffer; the pH and conductivity of the second elution buffer are/is greater than that of the first elution buffer.

13. The method of claim 12, characterized in that, the cation exchange medium is a filler having a functional group $SO_3^-$ which is bound to different substrates.

14. The method of claim 13, characterized in that, the cation exchange medium is at least one selected from the group consisting of carboxy-methyl-cellulose, sulphopropyl immobilized on agarose, sulphopropyl immobilized on polystyrene/divinyl benzene, sulfonyl immobilized on agarose, and sulphopropyl immobilized on hydrophilic polyacrylamides.

15. The method of claim 12, characterized in that, the first equilibration buffer is a salt-containing buffer, of which the buffer is 10-50 mmol/L acetic acid buffer, the salt is 40-60 mmol/L sodium chloride or ammonium sulfate, the pH is 4-6, and the conductivity is 8-13 ms/cm; the second equilibration buffer is a salt-free buffer, of which the buffer is 10-50 mmol/L acetic acid buffer, the pH is the same as that of the first equilibration buffer, and the conductivity is 1-2 ms/cm.

16. The method of claim 12, characterized in that, the change of pH of the wash buffer and the first elution buffer is achieved by adjusting the mixed ratio of two salt-containing buffers that have different pH, and achieved by changing 25% $Na_2HPO_4$ pH7.5+75% $Na_2HPO_4$ pH9.3-9.4 to 15% $Na_2HPO_4$ pH7.5+85% $Na_2HPO_4$ pH9.3-9.4.

17. The method of claim 12, characterized in that, the recombinant anti-HER2 antibody is selected from the group consisting of trastuzumab, pertuzumab and other HER2 antigen-binding recombinant antibodies.

18. The method of claim 12, characterized in that, the method further comprises subjecting the mixture comprising the recombinant anti-HER2 antibody and its related proteins to one or more purification steps, either before, during, or after the cation exchange chromatography, so as to obtain a homogeneous preparation of the recombinant anti-HER2 antibody.

* * * * *